US011241165B2

(12) United States Patent
Buesseler

(10) Patent No.: US 11,241,165 B2
(45) Date of Patent: Feb. 8, 2022

(54) MAGNETIC SENSOR FOR TRACKING THE LOCATION OF AN OBJECT

(71) Applicant: St. Jude Medical International Holding S.à r.l., Luxembourg (LU)

(72) Inventor: Ryan K. Buesseler, Delano, MN (US)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 364 days.

(21) Appl. No.: 16/210,469

(22) Filed: Dec. 5, 2018

(65) Prior Publication Data

US 2019/0167149 A1 Jun. 6, 2019

Related U.S. Application Data

(60) Provisional application No. 62/594,942, filed on Dec. 5, 2017.

(51) Int. Cl.
| | | |
|---|---|---|
| A61B 5/05 | (2021.01) | |
| A61B 5/06 | (2006.01) | |
| A61B 34/20 | (2016.01) | |
| A61B 18/14 | (2006.01) | |
| A61M 25/01 | (2006.01) | |
| A61B 5/00 | (2006.01) | |
| G01B 21/04 | (2006.01) | |
| G01B 7/04 | (2006.01) | |
| A61B 18/12 | (2006.01) | |
| A61B 18/00 | (2006.01) | |
| A61B 90/00 | (2016.01) | |
| A61B 5/287 | (2021.01) | |

(52) U.S. Cl.
CPC ............ *A61B 5/062* (2013.01); *A61B 5/063* (2013.01); *A61B 5/6852* (2013.01); *A61B 5/6869* (2013.01); *A61B 18/1492* (2013.01); *A61B 34/20* (2016.02); *A61M 25/0127* (2013.01); *G01B 7/046* (2013.01); *G01B 21/042* (2013.01); *A61B 5/065* (2013.01); *A61B 5/287* (2021.01); *A61B 18/1206* (2013.01); *A61B 90/37* (2016.02); *A61B 2018/00351* (2013.01); *A61B 2018/00577* (2013.01); *A61B 2018/00791* (2013.01); *A61B 2034/2051* (2016.02); *A61B 2034/2072* (2016.02); *A61B 2218/002* (2013.01); *A61B 2560/0223* (2013.01)

(58) Field of Classification Search
CPC combination set(s) only.
See application file for complete search history.

(56) References Cited

U.S. PATENT DOCUMENTS

| | | |
|---|---|---|
| 6,484,049 B1 | 11/2002 | Seeley et al. |
| 7,263,397 B2 | 8/2007 | Hauck et al. |
| 7,386,339 B2 | 6/2008 | Strommer et al. |
| 2012/0149966 A1* | 6/2012 | Ludwin .............. A61B 90/06 600/11 |
| 2013/0272592 A1 | 10/2013 | Eichler et al. |

\* cited by examiner

*Primary Examiner* — Joel F Brutus
(74) *Attorney, Agent, or Firm* — Dykema Gossett PLLC

(57) ABSTRACT

An apparatus for emitting a field comprising a core, a conductive winding with a first end, a second end, and an intermediate portion, where the conductive winding surrounds a portion of the core and is wound about a winding axis, a protrusion for aligning the apparatus where the protrusion is parallel with the winding axis, and a conductive connector extending from the conductive winding, wherein the conductive connector is electrically coupled with the conductive winding at the intermediate portion.

12 Claims, 12 Drawing Sheets

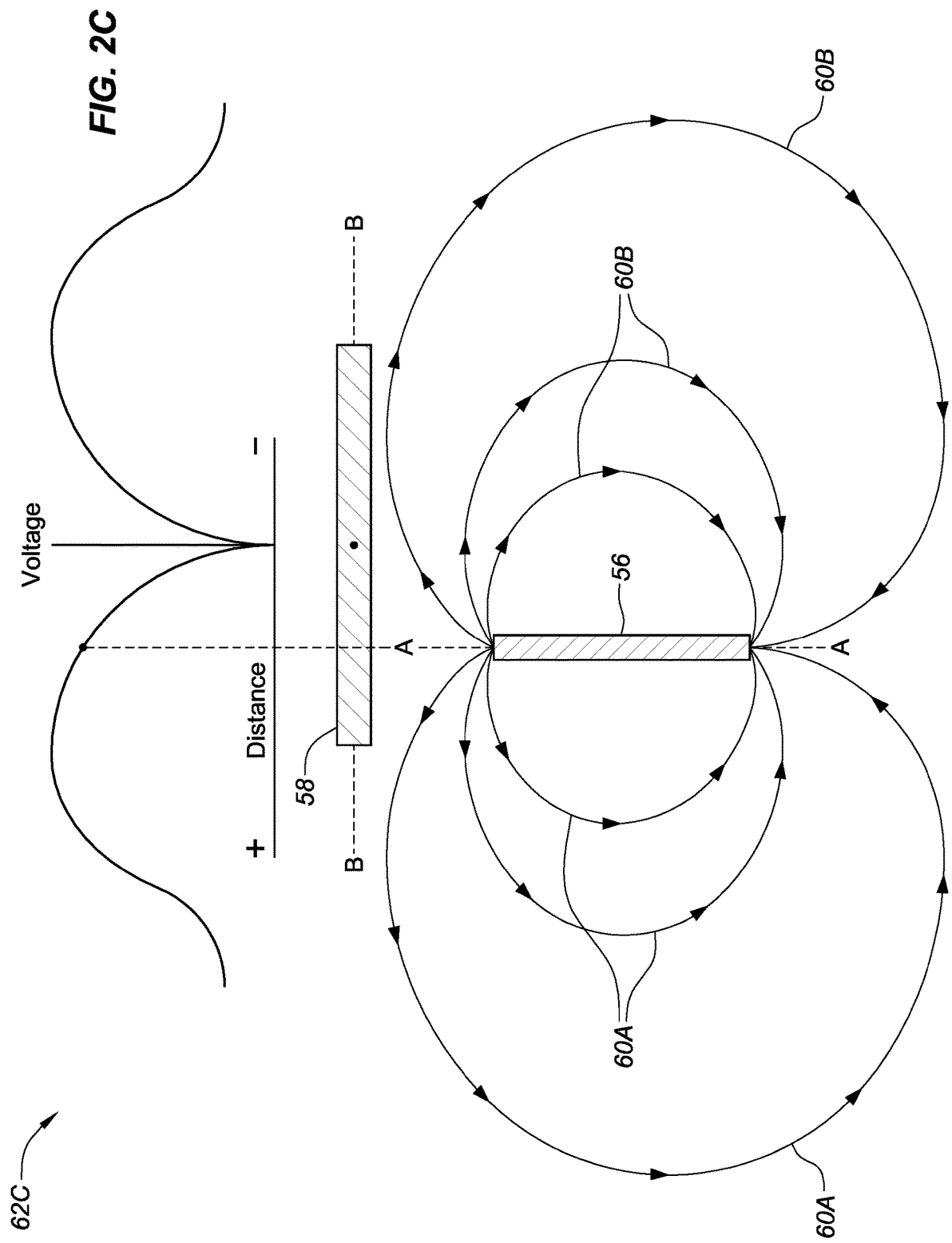

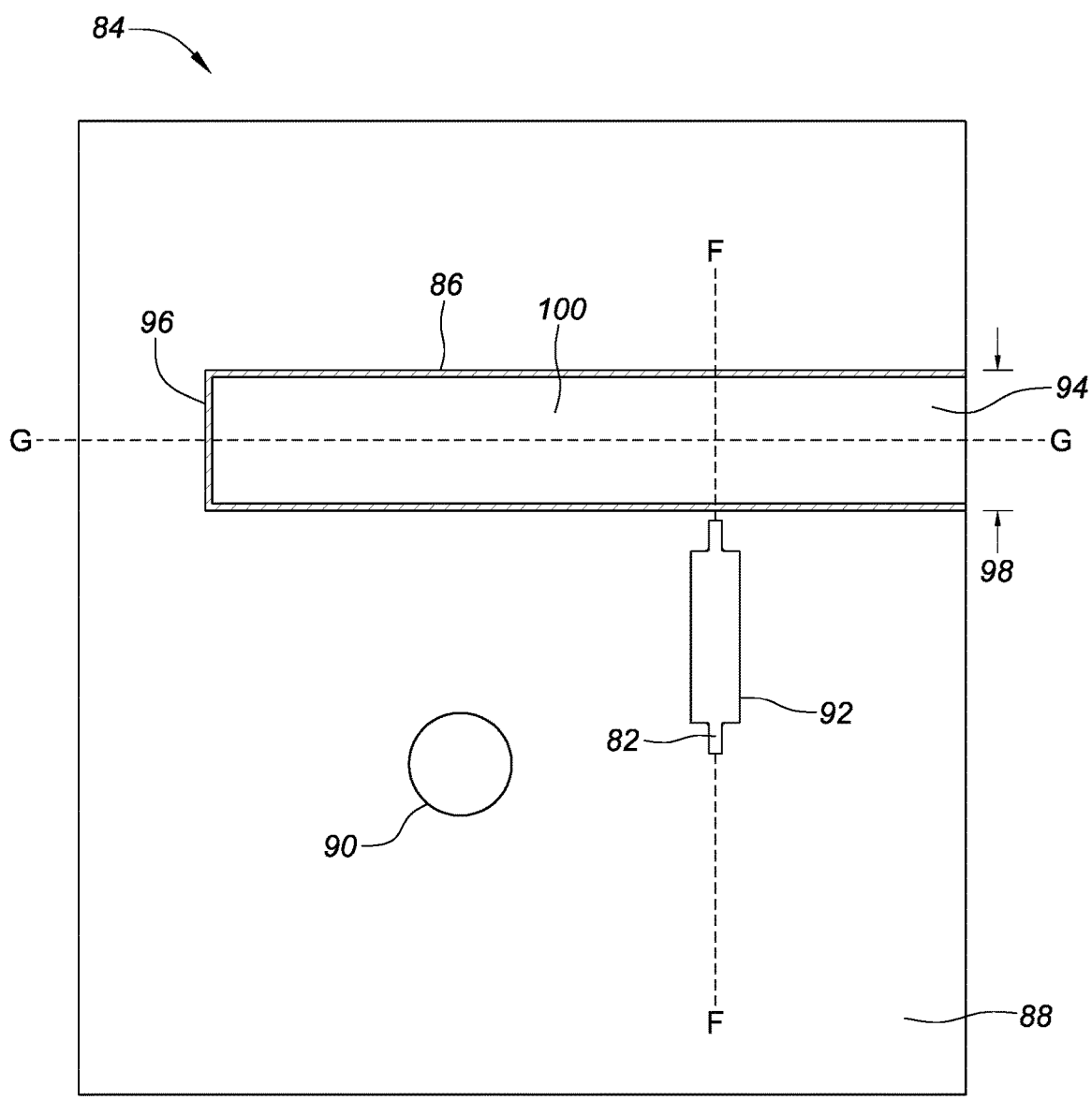
FIG. 7A₁
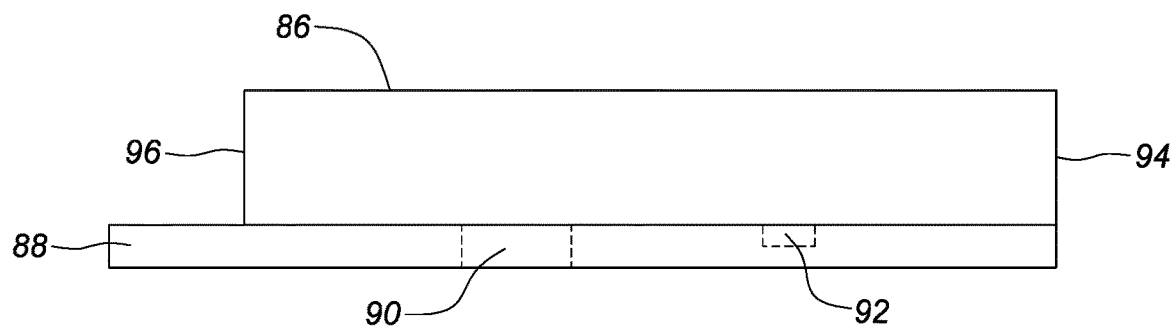
FIG. 7A₂

MAGNETIC SENSOR FOR TRACKING THE LOCATION OF AN OBJECT

CROSS-REFERENCE TO RELATED APPLICATIONS

This application claims the benefit of U.S. provisional application No. 62/594,942, filed 5 Dec. 2017 (the '942 application), which is hereby incorporated by reference as though fully set forth herein.

BACKGROUND a. Field

This disclosure relates to systems and apparatuses for tracking the location of an object. In particular, the instant disclosure relates to using a transducer and a sensor to track the location of a catheter relative to an introducer.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

To position a catheter at a desired site within the body, some type of navigation may be used, such as using mechanical steering features incorporated into the catheter (or an introducer). In some examples, medical personnel may manually manipulate and/or operate the catheter using the mechanical steering features.

In order to facilitate the advancement of catheters through a patient's vasculature, a navigating system may be used. Such navigating systems may include, for example, electric-field-based positioning and navigating systems that are able to determine the position and orientation of the catheter (and similar devices) within the body. In such electric-field-based positioning and navigating systems, it can be important to know and/or determine the distance between electrodes and/or other sensors and when electrodes and/or sensors on the catheter are shielded inside of a sheath or introducer that is being used to position the catheter at a desired location.

The foregoing discussion is intended only to illustrate the present field and should not be taken as disavowal of claim scope.

BRIEF SUMMARY

The instant disclosure, in at least one embodiment, comprises an apparatus for emitting a field comprising a core, a conductive winding with a first end, a second end, and an intermediate portion, where the conductive winding surrounds a portion of the core and is wound about a winding axis, a protrusion for aligning the apparatus where the protrusion is parallel with the winding axis, and a conductive connector extending from the conductive winding, wherein the conductive connector is electrically coupled with the conductive winding at the intermediate portion.

In another embodiment, a system comprises a first transducer assembly with a first longitudinal axis, the first transducer assembly comprising a core, a conductive winding, and a conductive connector electrically coupled with the conductive winding, wherein the core is parallel with the first longitudinal axis, a catheter with a second longitudinal axis, wherein the catheter comprises a first sensor, and a plurality of electrodes, where a location of the second sensor is known in relation to each of the plurality of electrodes, where the first longitudinal axis of the transducer assembly is perpendicular with the second longitudinal axis of the catheter, and an electronic control unit (ECU) electrically coupled to the first transducer assembly and the first sensor and operable to do the following: (A) generate a magnetic field using the first transducer assembly; (B) measure a first signal from the first sensor, wherein the first signal varies based on a position of the first sensor along the second longitudinal axis in relation to the magnetic field generated by the first transducer assembly; (C) analyze the first signal to determine a relative position of the catheter along the second longitudinal axis based on the location of the first sensor; (D) generate a relative position information for the catheter using the analysis of the first signal.

In another embodiment, a method for detecting a position of a sensor on an elongate medical device comprises positioning a catheter at a first location along a first longitudinal axis, emitting a field from a first transducer with a second longitudinal axis, where the first longitudinal axis is perpendicular with the second longitudinal axis, moving the catheter to a second position along the longitudinal axis, measuring a signal, by an electronic control unit (ECU) comprising a processor, at a first sensor on the catheter while moving the catheter along the longitudinal axis from the first position to the second position within the field, analyzing the signal, by the ECU, from the first sensor, and determining, by the ECU, a position data of the first sensor based on the signal.

BRIEF DESCRIPTION OF THE DRAWINGS

FIG. 2C is a schematic diagram of another exemplary embodiment of the first transducer and the first sensor of FIG. 2A, where the first transducer can be used to determine the location of the first sensor, in accordance with embodiments of the present disclosure.

FIG. $7A_1$ is a top partial cross-sectional view of an apparatus for measuring sensor spacing on an elongate medical device, where the apparatus includes a transducer that can be used for generating a field used for measuring the spacing on the elongate medical device, in accordance with embodiments of the present disclosure.

FIG. $7A_2$ is a side view of the fixture of FIG. $7A_1$, in accordance with embodiments of the present disclosure.

Figure 7B:
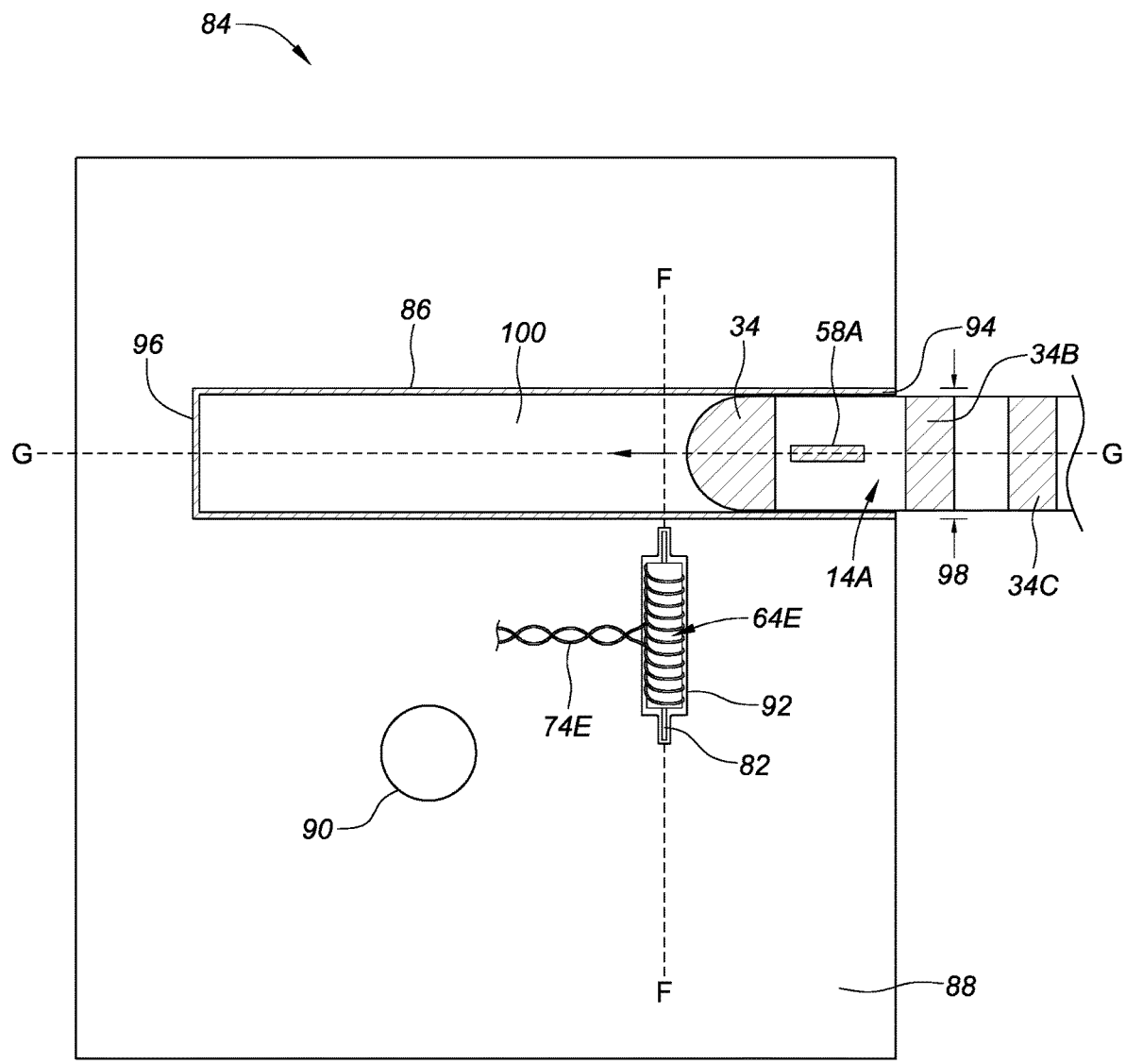

FIG. 7B is a schematic view of the apparatus of FIG. 7A with an exemplary catheter that includes a sensor mounted on a catheter, where the catheter is movable relative to the transducer assembly, in accordance with embodiments of the present disclosure.

Figure 7C:
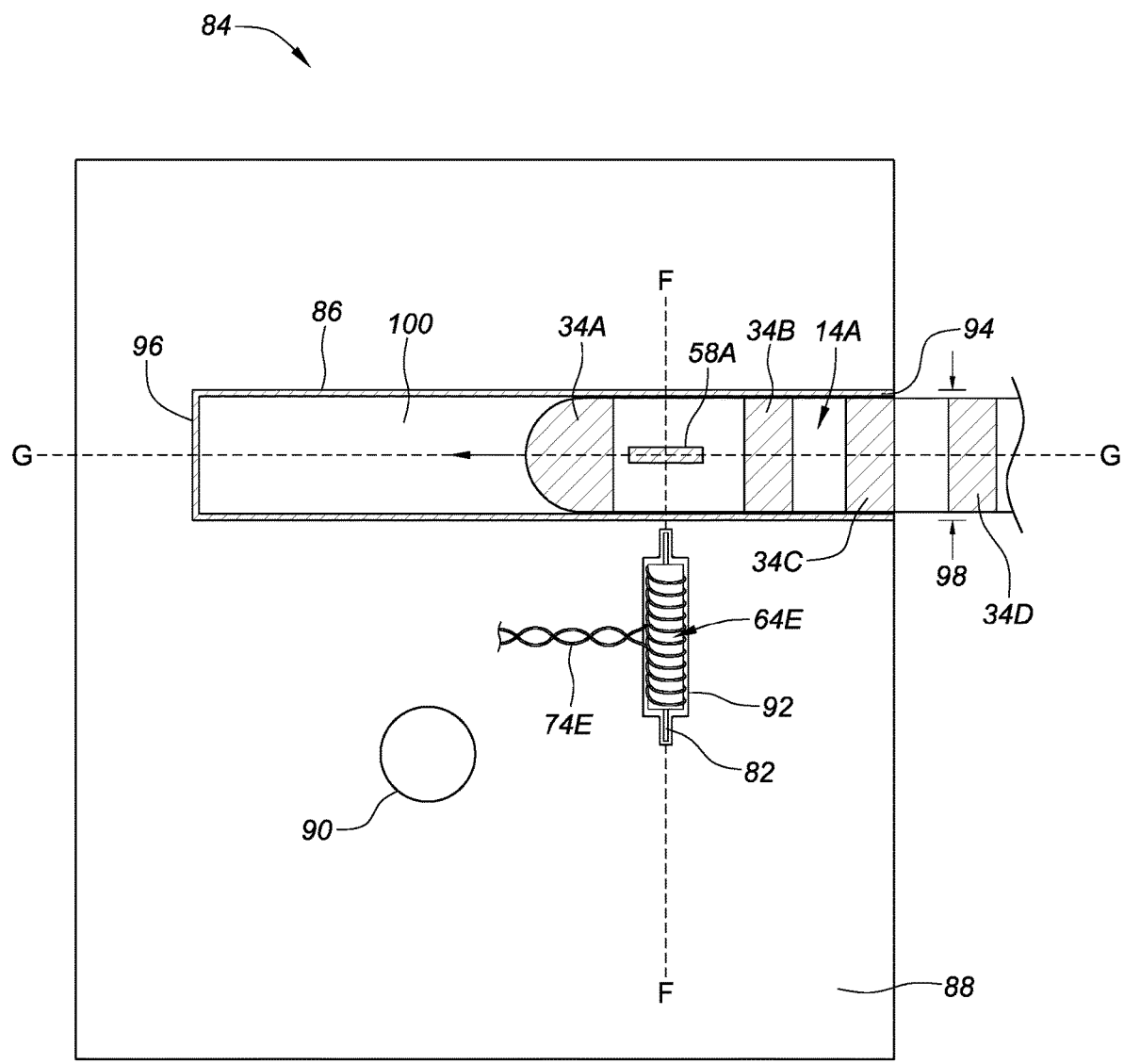

FIG. 7C is a schematic view of the apparatus of FIG. 7A with the exemplary catheter of FIG. 7B, where the catheter has moved relative to the transducer assembly, in accordance with embodiments of the present disclosure.

Figure 7D:
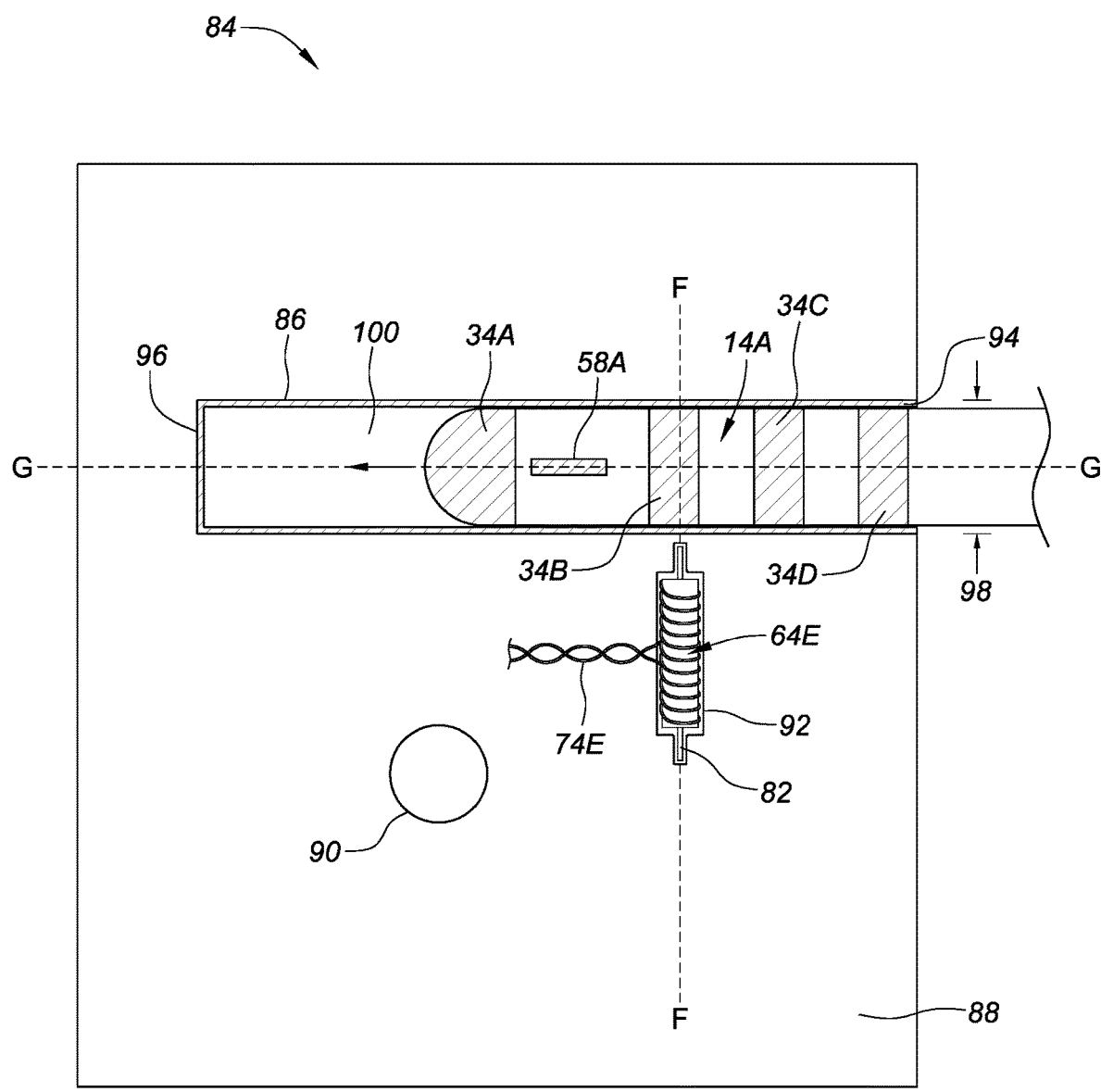

FIG. 7D is a schematic view of the apparatus of FIG. 7A with the exemplary catheter of FIGS. 7A-B, where the catheter has moved relative to the transducer assembly, in accordance with embodiments of the present disclosure.

Figure 8:
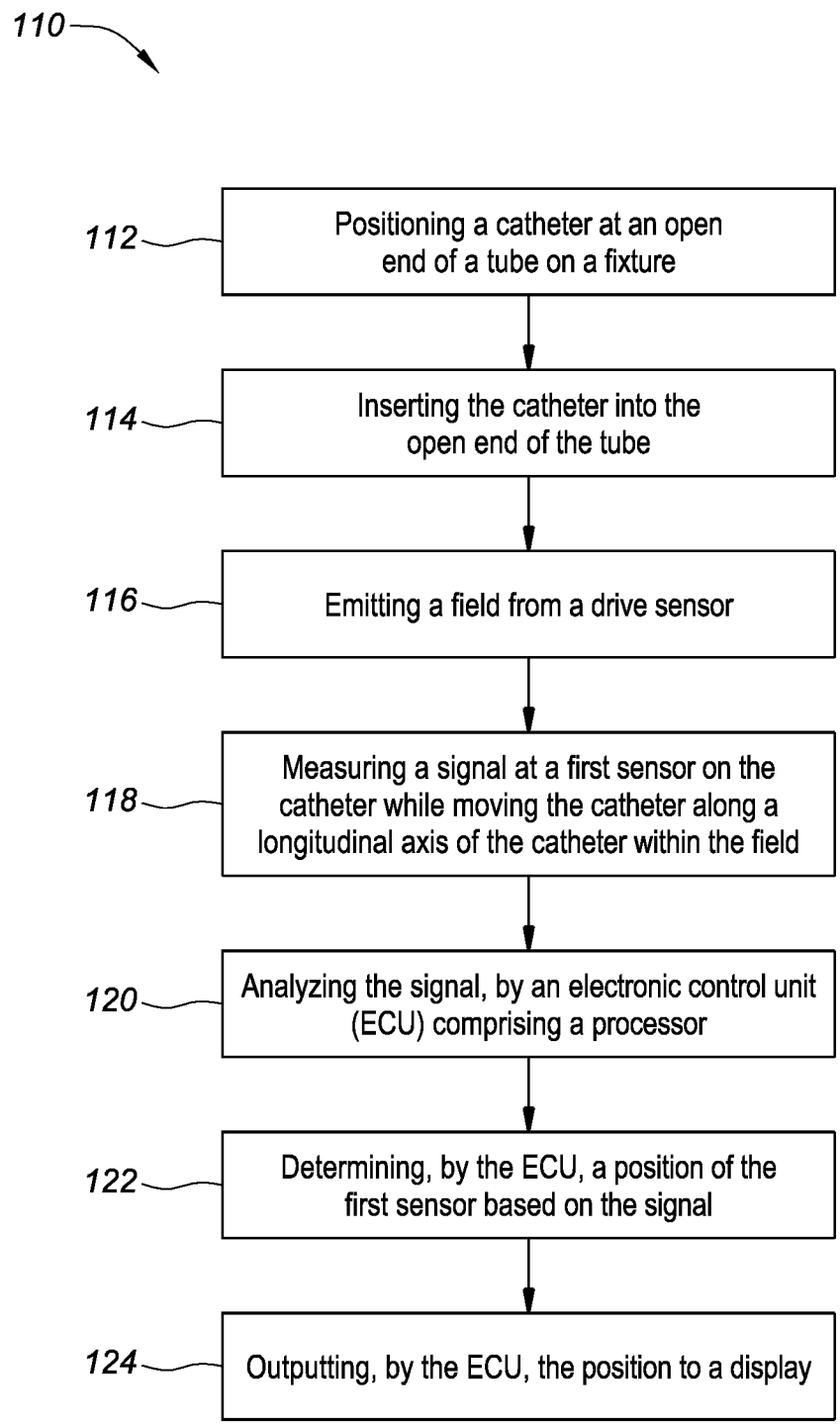

FIG. 8 is a diagram of steps in an exemplary method for measuring sensor spacing on an elongate medical device, in accordance with embodiments of the present disclosure.

Figure 9:
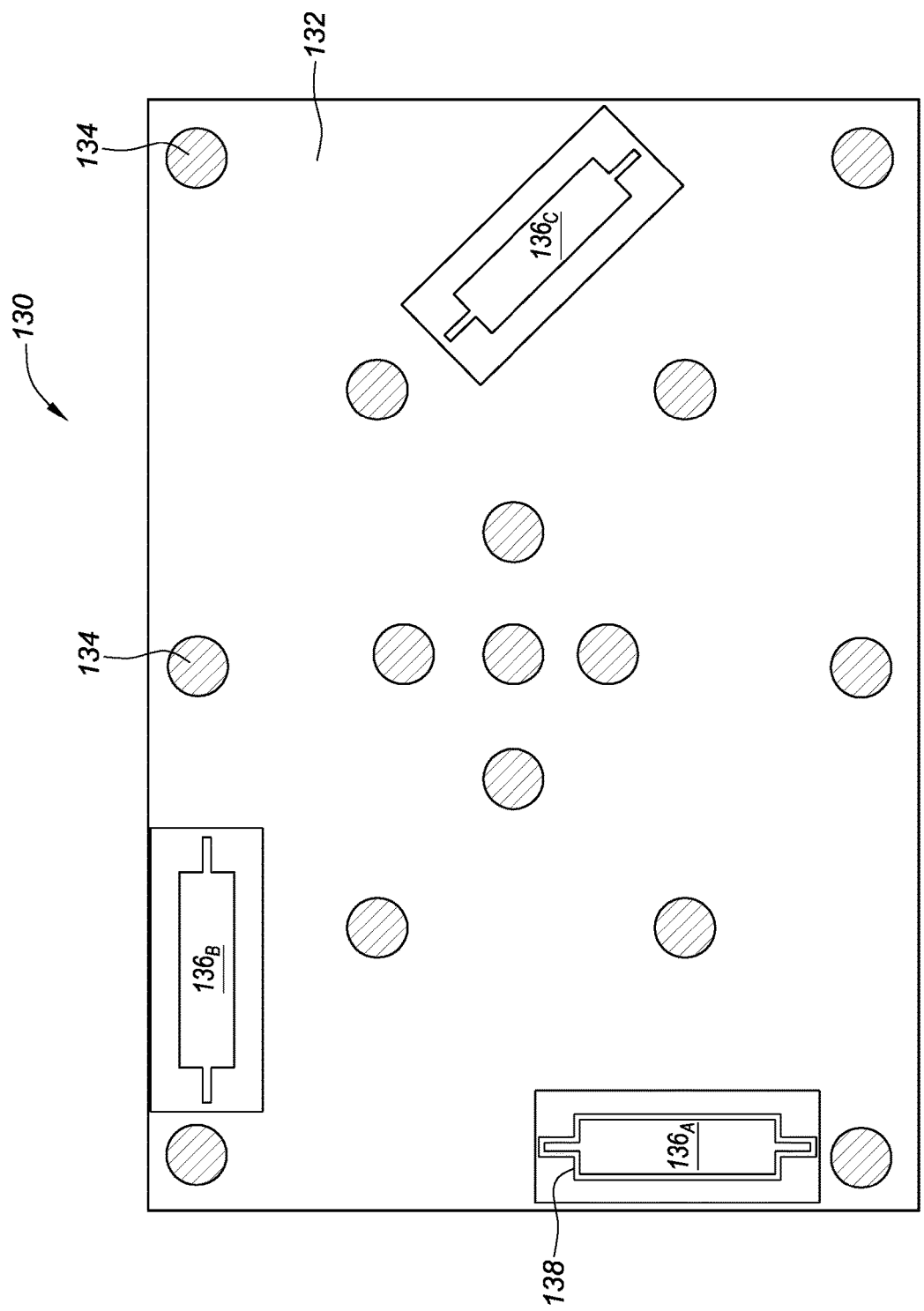

FIG. 9 is a schematic view of an optic-magnetic registration plate (OMRP), consistent with embodiments of the present disclosure.

DETAILED DESCRIPTION OF EMBODIMENTS

Figure 1:
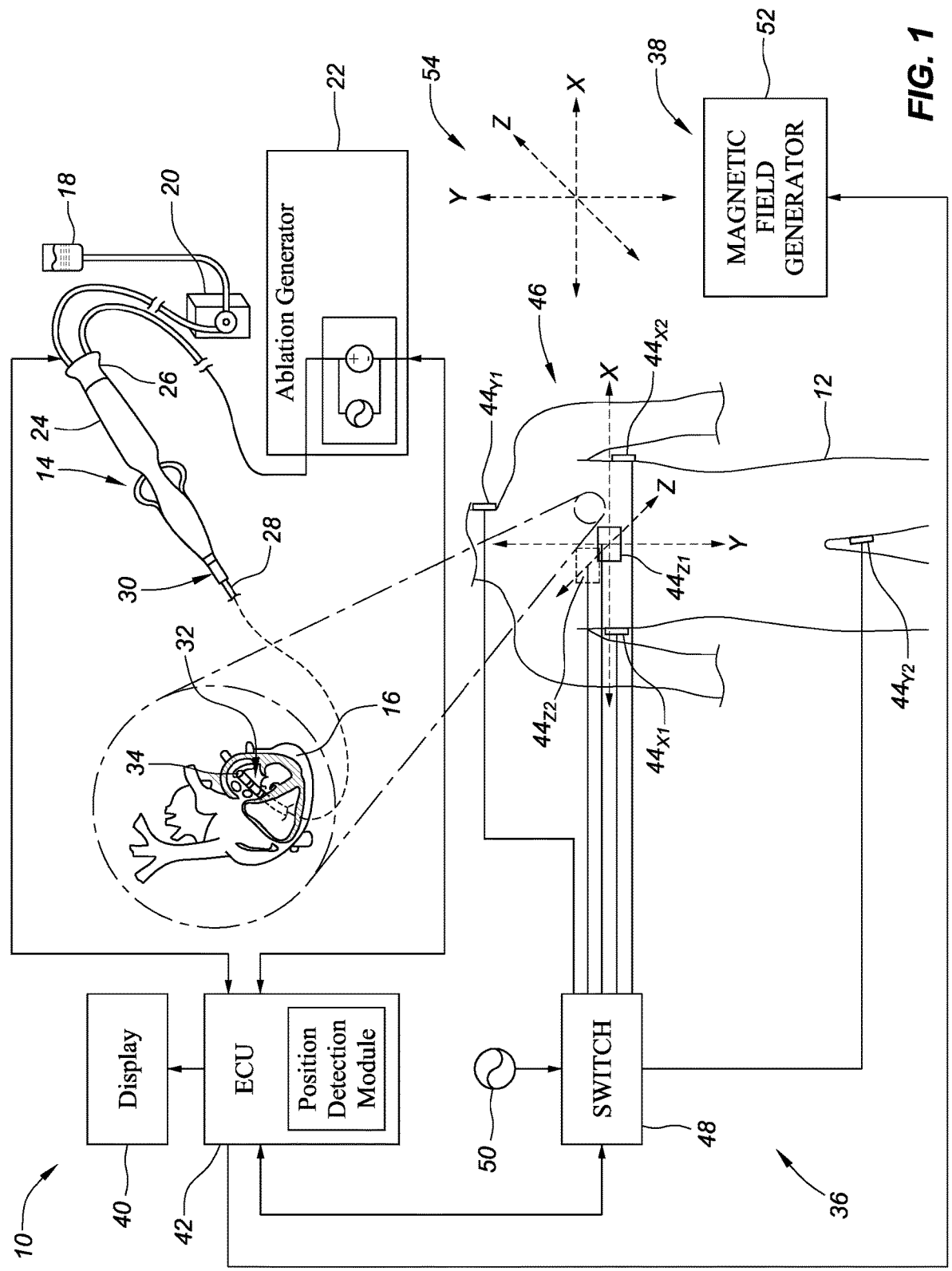
FIG. 1 is a system diagram showing a medical device and a medical positioning system, in accordance with embodiments of the present disclosure.

Referring now to the figures, in which like reference numerals refer to the same or similar features in the various views, FIG. 1 illustrates one embodiment of a system 10 for navigating a medical device within a body 12. In the illustrated embodiment, the medical device comprises a catheter 14 that is shown schematically entering a heart that has been exploded away from the body 12. The catheter 14, in this embodiment, is depicted as an irrigated radiofrequency (RF) ablation catheter for use in the treatment of cardiac tissue 16 in the body 12. It should be understood, however, that the system 10 may find application in connection with a wide variety of medical devices used within the body 12 for diagnosis or treatment. For example, the system 10 may be used to navigate an electrophysiological mapping catheter, an intracardiac echocardiography (ICE) catheter, or an ablation catheter using a different type of ablation energy (e.g., cryoablation, ultrasound, etc.). Further, it should be understood that the system 10 may be used to navigate medical devices used in the diagnosis or treatment of portions of the body 12 other than cardiac tissue 16. Further description of the systems and components are contained in U.S. patent application Ser. No. 13/839,963 filed on 15 Mar. 2013, which is hereby incorporated by reference in its entirety as though fully set forth herein.

Referring still to FIG. 1, the ablation catheter 14 is connected to a fluid source 18 for delivering a biocompatible irrigation fluid such as saline through a pump 20, which may comprise, for example, a fixed rate roller pump or variable volume syringe pump with a gravity feed supply from fluid source 18 as shown. The catheter 14 is also electrically connected to an ablation generator 22 for delivery of RF energy. The catheter 14 may include a handle 24; a cable connector or interface 26 at a proximal end of the handle 24; and a shaft 28 having a proximal end 30, a distal end 32, and one or more electrodes 34. The connector 26 provides mechanical, fluid, and electrical connections for conduits or cables extending from the pump 20 and the ablation generator 22. The catheter 14 may also include other conventional components not illustrated herein such as a temperature sensor, additional electrodes, and corresponding conductors or leads.

The handle 24 provides a location for the physician to hold the catheter 14 and may further provide means for steering or guiding the shaft 28 within the body 12. For example, the handle 24 may include means to change the length of one or more pull wires extending through the catheter 14 from the handle 24 to the distal end 32 of shaft 28. The construction of the handle 24 may vary.

The shaft 28 may be made from conventional materials such as polyurethane and may define one or more lumens configured to house and/or transport electrical conductors, fluids, or surgical tools. The shaft 28 may be introduced into a blood vessel or other structure within the body 12 through a conventional introducer. The shaft 28 may then be steered or guided through the body 12 to a desired location such as the tissue 16 using guide wires or pull wires or other means known in the art including remote control guidance systems. The shaft 28 may also permit transport, delivery, and/or removal of fluids (including irrigation fluids and bodily fluids), medicines, and/or surgical tools or instruments. It should be noted that any number of methods can be used to introduce the shaft 28 to areas within the body 12. This can include introducers, sheaths, guide sheaths, guide members, guide wires, or other similar devices. For ease of discussion, the term introducer will be used throughout.

The system 10 may include an electric-field-based positioning system 36, a magnetic-field-based positioning system 38, a display 40, and an electronic control unit (ECU) 42 (e.g., a processor). Each of the exemplary system components is described further below.

The electric-field-based positioning system 36 and the magnetic-field-based positioning system 38 are provided to determine the position and orientation of the catheter 14 and similar devices within the body 12. The position and orientation of the catheter 14 and similar devices within the body 12 can be determined by the system 36 and/or the system 38. The system 36 may comprise, for example, the EnSite™ NavX™ system sold by St. Jude Medical, Inc. of St. Paul, Minn., and described in, for example, U.S. Pat. No. 7,263,397 titled "Method and Apparatus for Catheter Navigation and Location Mapping in the Heart," the entire disclosure of which is hereby incorporated by reference as though fully set forth herein. The systems 36 and 38 may comprise, for example, the EnSite Precision™ system sold by St. Jude Medical, Inc., of St. Paul, Minn. The system 36 operates based upon the principle that when low amplitude electrical signals are passed through the thorax, the body 12 acts as a voltage divider (or potentiometer or rheostat) such that the electrical potential or field strength measured at one or more electrodes 34 on the catheter 14 may be used to determine the position of the electrodes, and, therefore, of the catheter 14, relative to a pair of external patch electrodes using Ohm's law and the relative location of a reference electrode (e.g., in the coronary sinus).

In the configuration is shown in FIG. 1, the electric-field-based positioning system 36 further includes three pairs of patch electrodes 44, which are provided to generate electrical signals used in determining the position of the catheter 14 within a three-dimensional coordinate system 46. The electrodes 44 may also be used to generate EP data regarding the tissue 16. To create axes-specific electric fields within body 12, the patch electrodes are placed on opposed surfaces of the body 12 (e.g., chest and back, left and right sides of the thorax, and neck and leg) and form generally orthogonal x, y, and z axes. A reference electrode/patch (not shown) is typically placed near the stomach and provides a reference value and acts as the origin of the coordinate system 46 for the navigation system.

In accordance with this exemplary system 36 as depicted in FIG. 1, the patch electrodes include right side patch $44_{X1}$, left side patch $44_{X2}$, neck patch $44_{Y1}$, leg patch $44_{Y2}$, chest patch $44_{Z1}$, and back patch $44_{Z2}$; and each patch electrode is connected to a switch 48 (e.g., a multiplex switch) and a signal generator 50. The patch electrodes $44_{X1}$, $44_{X2}$ are placed along a first (x) axis; the patch electrodes $44_{Y1}$, $44_{Y2}$ are placed along a second (y) axis, and the patch electrodes $44_{Z1}$, $44_{Z2}$ are placed along a third (z) axis. Sinusoidal currents are driven through each pair of patch electrodes, and voltage measurements for one or more position sensors (e.g., ring electrodes 34 or a tip electrode located near the distal end 32 of catheter shaft 28) associated with the catheter 14 are obtained. The measured voltages are a function of the distance of the position sensors from the patch electrodes. The measured voltages are compared to the potential at the reference electrode and a position of the position sensors within the coordinate system 46 of the navigation system is determined.

The magnetic-field-based positioning system 38 in this exemplary embodiment employs magnetic fields to detect the position and orientation of the catheter 14 within the body 12. The system 38 may include the GMPS system made available by MediGuide, Ltd. and generally shown and described in, for example, U.S. Pat. No. 7,386,339 titled "Medical Imaging and Navigation System," the entire disclosure of which is hereby incorporated by reference as though fully set forth herein. In such a system, a magnetic field generator 52 may be employed having three orthogonally arranged coils (not shown) to create a magnetic field within the body 12 and to control the strength, orientation, and frequency of the field. The magnetic field generator 52 may be located above or below the patient (e.g., under a patient table) or in another appropriate location. Magnetic fields are generated by the coils and current or voltage measurements for one or more position sensors (not shown) associated with the catheter 14 are obtained. The measured currents or voltages are proportional to the distance of the sensors from the coils, thereby allowing determination of a position of the sensors within a coordinate system 54 of system 38.

The display 40 is provided to convey information to a physician to assist in diagnosis and treatment. The display 40 may comprise one or more conventional computer monitors or other display devices. The display 40 may present a graphical user interface (GUI) to the physician. The GUI may include a variety of information including, for example, an image of the geometry of the tissue 16, electrophysiology data associated with the tissue 16, graphs illustrating voltage levels over time for various electrodes 34, and images of the catheter 14 and other medical devices and related information indicative of the position of the catheter 14 and other devices relative to the tissue 16.

The ECU 42 provides a means for controlling the operation of various components of the system 10, including the catheter 14, the ablation generator 22, and magnetic generator 52 of the magnetic-field-based positioning system 38. The ECU 42 may also provide a means for determining the geometry of the tissue 16, electrophysiology characteristics of the tissue 16, and the position and orientation of the catheter 14 relative to tissue 16 and the body 12. The ECU 42 also provides a means for generating display signals used to control the display 40.

As the catheter 14 moves within the body 12, and within the electric field generated by the electric-field-based positioning system 36, the voltage readings from the electrodes 34 change, thereby indicating the location of catheter 14 within the electric field and within the coordinate system 46 established by the system 36. The ring electrodes 34 communicate position signals to ECU 42 through a conventional interface (not shown). In order to avoid introducing undesirable shift or drift into the determined catheter position and orientation based upon readings obtained by the electric-field based positioning system 36, it can be important to know when the catheter electrodes 34 are inside the introducer. In particular, if the catheter electrodes 34 are located inside the introducer, the data coming off of those shielded electrodes may be degraded/compromised.

Figure 2A:
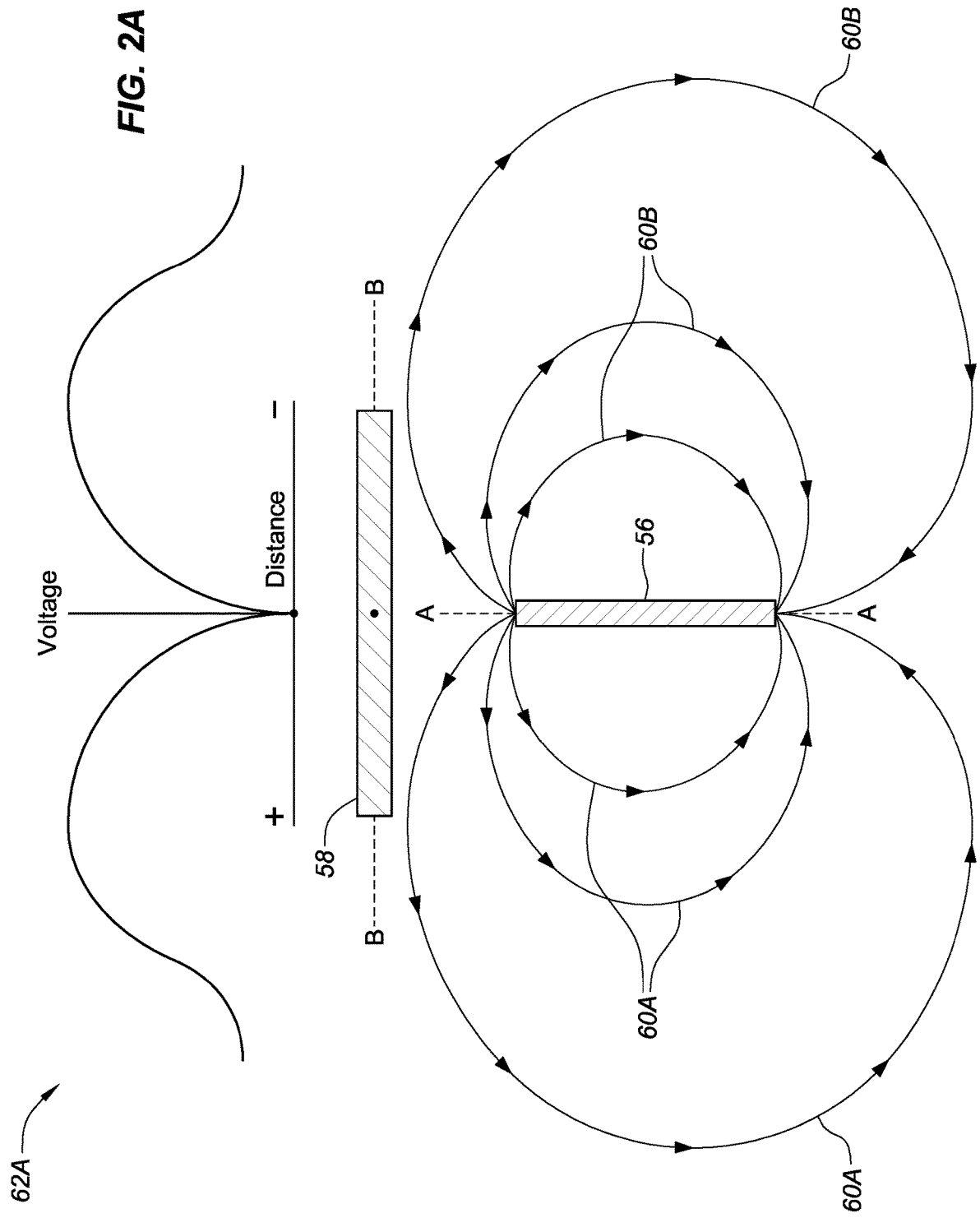
FIG. 2A is a schematic diagram of a first transducer and a first sensor, where the first transducer can be used to determine the location of the first sensor, in accordance with embodiments of the present disclosure.

FIG. 2A is a schematic diagram of a first transducer (e.g., an emitter) 56 and a first sensor 58, where the first transducer 56 can be used to determine the location of the first sensor 58, in accordance with embodiments of the present disclosure. The first transducer 56 can have a first longitudinal axis represented by a line A-A. The first sensor 58 can have a second longitudinal axis represented by a line B-B. The first transducer 56 can be positioned with the first longitudinal axis at an angle with respect to a second longitudinal axis represented by a line B-B of the first sensor 58. For example, the angle between the lines A-A and B-B can be 90°.

The first transducer 56 can be used to generate, for example, a magnetic field 60A-B (e.g., the first transducer 56 can be a coil or a magnetic field generator similar to magnetic generator 52 (e.g., a "drive coil")). Other embodiments of the transducer can emit other electro-magnetic fields. The magnetic field 60A-B can be used to determine a position of the first sensor 58. The magnetic field 60A-B generated can have various field lines as shown in FIG. 2A. The magnetic field 60A-B can generate zero (0) voltage, as measured across the first sensor 58, when the first sensor 58 is in a specific position (e.g., the center (longitudinally) of the first sensor 58 is aligned with a longitudinal axis of the first transducer 56).

In some embodiments, the first transducer 56 and the first sensor 58 can be the same physical structure (e.g., same size, same components/elements) where the difference is how the two are used. In that embodiment, the first transducer 56 can be used to generate a field (e.g., a magnetic field) and the first sensor 58 can be used to sense the field (e.g., measure a voltage across the first sensor 58). In another embodiment, the functions could be reversed (e.g., the first sensor 58 could be used to generate a field (e.g., a magnetic field) and the first transducer 56 could be used to sense the field (e.g., measure a voltage across the first transducer 56).

For example, the magnetic field 60A-B can be positioned such that a voltage can be measured across the first sensor 58, and that voltage can convey the location of the first sensor 58 within the magnetic field and along the longitudinal axis represented by the line B-B. For example, the voltage can be analyzed to determine the location of the second sensor. When the center of the first sensor 58 is to the left of the longitudinal axis in magnetic field 60A, represented by the line A-A, of the first sensor, the voltage measured can be a positive voltage value (see FIG. 2B and related discussion). When the first sensor 58 is centered in the field as shown in FIG. 2A, the voltage measured across the first sensor 58 can be zero or close to zero. When the center of the first sensor 58 is to the right of the longitudinal axis in magnetic field 60B, represented by the line A-A, of the first transducer 56, the voltage measured across the first sensor 58 can be a positive voltage value measured across the first sensor 58 (see FIG. 2C and related discussion). Electrical current can flow either way through the first transducer 56 and a positive voltage will still be measured across the first sensor 58. A change in current direction will produce a phase shift and a polarity shift.

A corresponding graph 62A in FIG. 2A shows the relationship of distance represented as x-axis (e.g., a position) to voltage represented as y-axis, as measured across the first sensor 58, for first transducer 56 with respect to the first sensor 58 (as measured by movement/change of position by the first sensor 58 along the longitudinal axis B-B). As shown in FIG. 2A and the graph 62A, when the first sensor 58 is centered on the first transducer 56, the voltage can be zero. Moving the first sensor 58 in relation to the first transducer 56 (e.g., left or right) can cause a change in the measured voltage for the first sensor 58. For example, moving the first sensor 58 to the left in magnetic field 60A can cause the voltage to increase (e.g., a greater positive voltage value as you move left) for the first sensor 58 (e.g., see FIG. 2B). Moving the second sensor to the right in magnetic field 60B can cause the voltage to increase (a larger positive voltage value as you move right) for the first sensor 58 (e.g., see FIG. 2C). The voltage measured across the first sensor 58 can vary when the first sensor 58 is moved along the longitudinal axis B-B. The voltage can be positive for movement to the left and the right of the centerline of graph 62A because of a phase shift in the voltage.

Information about the position and/or movement of the first sensor 58 with respect to the first transducer 56 can be used by, for example, a position detection module that is part of the ECU to determine a position and/or movement of, for example, the distal end 32 (FIG. 1) of the catheter 14 (FIG. 1) in relation to a distal end of an introducer because of a known position of the first sensor 58 with relation to the distal end 32 of the catheter 14. In some embodiments, the position detection module can be provided as part of the electric-field-based positioning system 36 (FIG. 1) and/or the magnetic-field-based positioning system 38 (e.g., as part of the ECU 42 of FIG. 1). See FIGS. 7A-D and related discussion below for more information.

The position detection module can include, for example, a processor and a memory storing non-transitory computer-readable instructions, as discussed herein (e.g., as part of the ECU 42, or a separate processor and a separate memory, or a combination of the two). The ECU 42 may be programmed with a computer program (e.g., software) encoded on a computer-readable storage medium for assessing the distances between an electrode (e.g., electrode 34 of FIG. 1) and one or more sensors (e.g., the first transducer 56 and the first sensor 58). The instructions can be executable to compute, for example, the amount of movement and/or position(s) of the distal end 32 (e.g., an electrode 34 of FIG. 1, as a distance between the first sensor 58 and the electrode 34 can be known/determined) of the shaft 28 (FIG. 1) of the catheter 14 and the distal end of the introducer, the rate of change in the distances/movement, or other characteristics related to the position of the distal end 32 of the shaft 28 of the catheter 14 in relation to the distal end of the introducer. The distance between various electrodes 34 (FIG. 1) can be known from previous measurements (e.g., determined during/after manufacturing of the catheter and included with the catheter) or the distance between various electrodes and/or sensors can be determined and described herein. The program can include code for calculating a value responsive to magnitudes of, for example, a voltage between the first transducer 56 and the first sensor 58.

It should be understood that the system 10 (of FIG. 1), particularly ECU 42, as described above may include conventional processing apparatus known in the art, capable of executing pre-programmed instructions stored in an associated memory, all performing in accordance with the functionality described herein. It is contemplated that the methods described herein, including without limitation the method steps of embodiments of the disclosure, will be programmed in a preferred embodiment, with the resulting software being stored in an associated memory and where so described, may also constitute the means for performing such methods. Implementation of the embodiments, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Figure 2B:
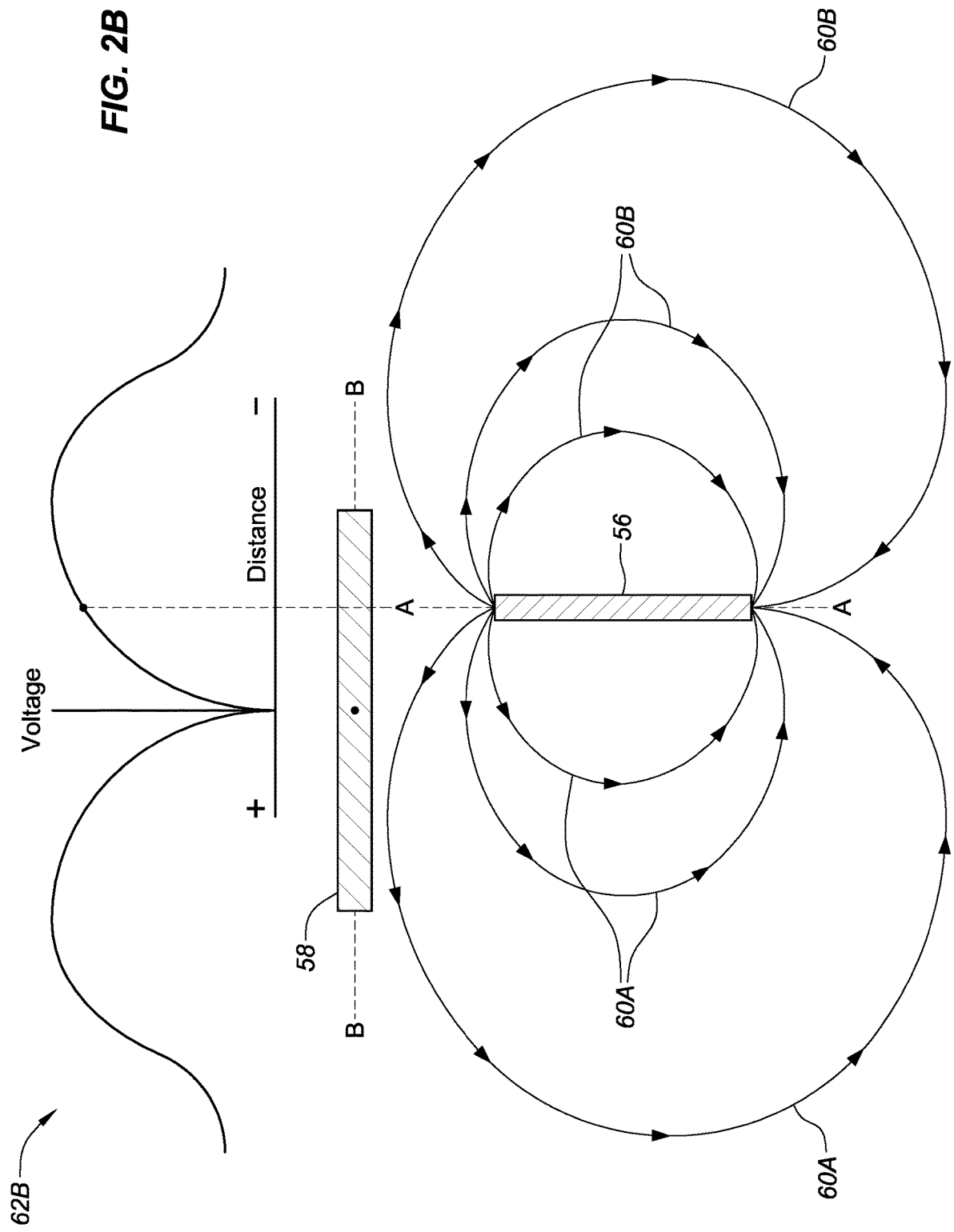
FIG. 2B is a schematic diagram of an exemplary embodiment of the first transducer and the first sensor of FIG. 2A, where the first transducer can be used to determine the location of the first sensor, in accordance with embodiments of the present disclosure.

FIG. 2B is a schematic diagram of an exemplary embodiment of the first transducer 56 and the first sensor 58 of FIG. 2A, where the first transducer 56 can be used to determine the location of the first sensor 58, in accordance with embodiments of the present disclosure. A corresponding graph 62B in FIG. 2B shows the relationship of distance (e.g., a position) to voltage for the first transducer 56 and the first sensor 58. As shown in FIG. 2B and the graph 62B, when the center of the first sensor 58 is to the left of the center on the first transducer 56 (in magnetic field 60A), the voltage, as measured across the first sensor 58, can be a positive voltage value. (e.g., a larger positive voltage value as the first sensor 58 is moved left in FIG. 2B) for the second sensor. As the magnetic sensor 58 is moved left (or sensor 56 is moved right, this is essentially the same thing), more of the flux lines 60A are able to move through the core—thereby creating more voltage. Any time there are flux lines 60A and 60B that can intercept the core at the same time, they work to cancel each other out, thereby reducing the voltage from its maximum potential.

FIG. 2C is a schematic diagram of another exemplary embodiment of the first transducer 56 and the first sensor 58 of FIG. 2A, where the first transducer 56 can be used to determine the location of the first sensor 58, in accordance with embodiments of the present disclosure. A corresponding graph 62C in FIG. 2C shows the relationship of distance (e.g., a position) to voltage for the first transducer 56 and the first sensor 58. As shown in FIG. 2C and the graph 62C, when the first sensor 58 is to the right of the center on the first transducer 56 (in magnetic field 60B), the voltage, as measured across the first sensor 58, can be positive (a larger positive voltage value as the first sensor 58 is moved right in FIG. 2C) for the first sensor 58 (see above discussion for additional detail).

Figure 3:
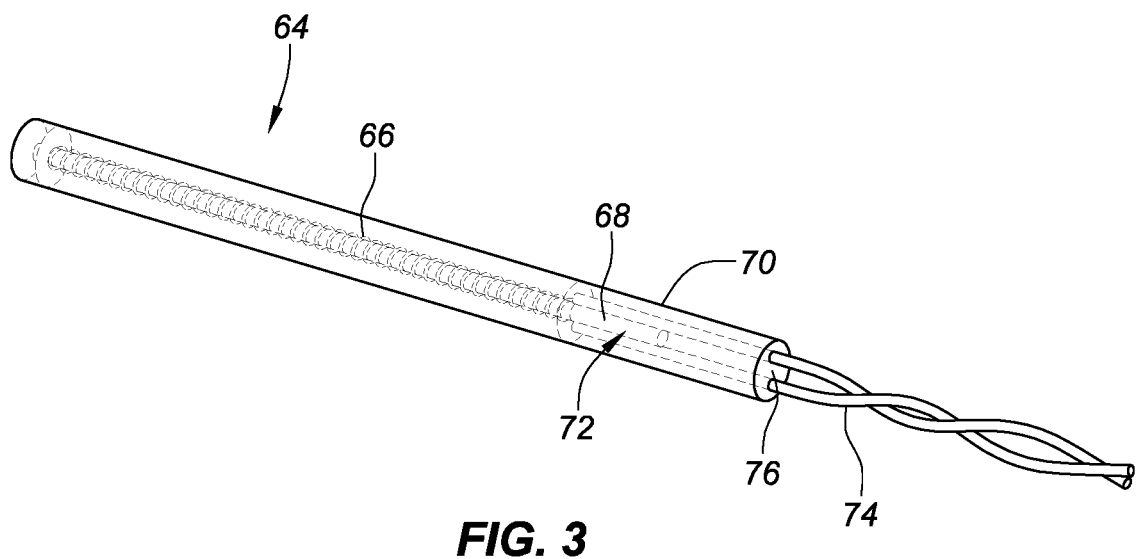
FIG. 3 is a schematic diagram of a transducer assembly that can be used for locating a position of a medical device, in accordance with embodiments of the present disclosure.

FIG. 3 is a schematic diagram of a transducer assembly 64 that can be used for locating a position of a medical device, in accordance with embodiments of the present disclosure. The transducer assembly 64 can include a conductive winding (e.g., a coil) 66, a core 68, a tube 70, a coating 72 disposed on and/or surrounding the core 68, a conductive connector (e.g., a pair of wires) 74, and a tube end 76. In some embodiments, the transducer assembly 64 can be considered a "drive coil" (e.g., used to create a magnetic field; similar to the first transducer 56 in FIGS. 2A-C) for a another sensor (e.g., a "sensing" sensor; similar to the first sensor 58 in FIGS. 2A-C). The coating 72 on and/or surrounding the core 68 can be any suitable material including for example, an adhesive, a polymer (e.g., polyimide, fluorinated ethylene propylene, heat shrink (e.g., nylon, polyolefin), a metal, etc. The coating 72 can be used to create the size and/or shape of the sensor assembly. For example, the thicker the layer of the coating 72 (e.g., as measured radially from the core 68) the larger the diameter of the core/coil/coating portion of the transducer assembly 64. The coating 72 can cover all of the coil 66 or a portion of the coil 66. The coating 72 can be the same thickness as shown in FIG. 3 (e.g., as measured radially from the core 68) or it can have varying thickness at different portions along the core 68 (e.g., see FIG. 5 and related discussion). The pair of wires 74 can be, in some embodiments, a twisted pair of wires as shown in FIG. 3. The pair of wires 74 can be used to electrically couple the transducer assembly 64 to a power supply and/or to an electronic control unit (e.g., ECU 42).

The transducer assembly 64 can be used to generate a field (e.g., a magnetic field similar to the field shown in FIGS. 2A-C and described above). The field can be used for tracking the location of another sensor. Placement of the transducer assembly 64 is one factor that can affect the accuracy of the tracking of the location of the other sensor. As described above, aligning the transducer assembly 64 so that a longitudinal axis of the first transducer 56 is perpendicular to the path of movement that the first sensor 58 travels can provide more accurate information about the position of the first sensor 58 that is moving/changing position relative to the first transducer 56 (the drive coil).

Misalignment between a longitudinal axis (e.g., line C-C) of the sensor (e.g., the coil 62A and the core 64A) and the longitudinal axis (e.g., line D-D) of the sensor assembly (e.g., the tube) (e.g., the sensor is not "straight" inside the sensor assembly; see FIG. 4 and below for more information) can introduce variations in the information between the actual location of the second sensor and the estimated location as the second sensor changes position/moves. For example, manufacturing tolerances can cause the tube 70 can be large enough to cause up to 0.5° angulation between the longitudinal axis of the tube 70 and the longitudinal axis of the coil 66 and the core 68. This angulation can lead to issues (e.g., errors) in accurately detecting the position of sensors (e.g., inside catheters or other locations). For example, a misalignment of the coil and core of the first transducer 56 (FIG. 2A) can lead to an erroneous voltage (graph 62A) for a given position of the first sensor 58. See additional discussion below related to FIG. 4 for additional information.

Figure 4:
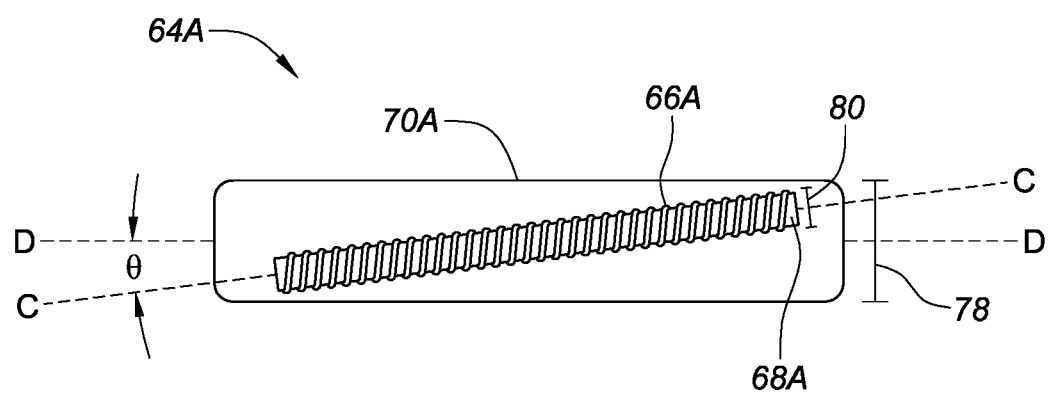
FIG. 4 is a schematic diagram of a transducer assembly, in accordance with embodiments of the present disclosure.

FIG. 4 is a schematic diagram of a transducer assembly 64A, in accordance with embodiments of the present disclosure. A transducer assembly 64A can include a coil 66A, a core 68A and a tube 70A where the coil 66A and the core 64A can be coupled internally with a tube 70A similar to FIG. 3. The coil 66A and the core 68A can be coupled with the tube 70A through any suitable method, including a friction fit and/or adhesive. A diameter 74 of the tube 74A can be sized to be slightly larger than a diameter of the coil 66A and the core 68A. The coil 66A can be a winding (e.g., of wire) wrapped around the core 68A.

In some instances, it is desirable to have a longitudinal axis of the coil 66A and the core 68A, represented by the line C-C align with a longitudinal axis of the tube 70A, represented by the line D-D. The alignment of the two longitudinal axes C-C and D-D can allow for more accurate evaluation of the position of second sensor (e.g., first sensor 58 of FIG. 2A-) with respect to the transducer assembly 64A (e.g., first transducer 56 of FIGS. 2A-C). However, because of, for example, variations in the sizes of the coil 66A, the core 68A (e.g., a diameter 80 of the coil and core together), and a diameter 78 of the tube 70A, it is possible for the longitudinal axis of the coil 66A and the core 68A (represented by the line C-C) to be offset by an angle θ from the longitudinal axis of the tube 70A (represented by the line D-D) as shown in FIG. 4. As discussed above, the offset represented by the angle θ can cause up to 0.5° of angulation between the longitudinal axis of the tube 70A and the longitudinal axis of the coil 66A and the core 68A which can lead to errors in determining a location/position of a second sensor (e.g., transducer assembly 64A) with respect to a first transducer (a drive coil).

Figure 5:
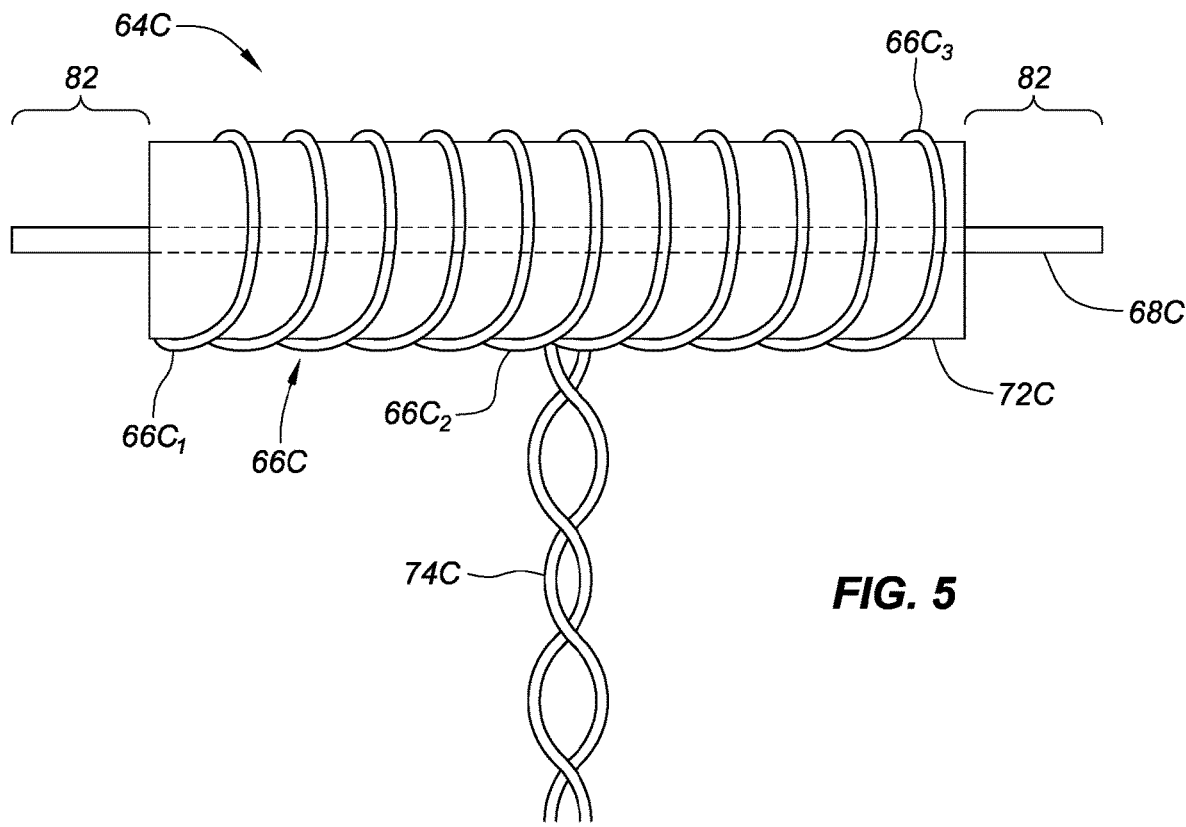
FIG. 5 is a side view of a transducer assembly that can be used for locating and/or tracking a position of a medical device, in accordance with embodiments of the present disclosure.

FIG. 5 is a side view of an transducer assembly 64C that can be used for locating and/or tracking a position of a medical device, in accordance with embodiments of the present disclosure. The transducer assembly 64C can include a coil 66C, a core 68C, a coating 72C, and a pair of wires 74C. The coil 66C can have a first end $66C_1$, a second end $66C_3$, and an intermediate portion $66C_2$ and can be a wire wound around the a portion of the core 68C (directly or indirectly) in a generally concentric pattern (although any suitable pattern can be used, which could differ from the exemplary arrangement shown in FIG. 5). The pair of wires 74C can connect to the coil 66C at the intermediate portion of the coil 66C allowing for easier alignment/placement of the coil 66C. The pair of wires 74C can be integral to the coil 66C (e.g., each wire of the pair of wires 74C is separately wound around the core 68C making the pair of wires 74C and the coil 66C the same element) or the pair of wires 74C can be separate and coupled with the coil 66C (e.g., soldered or otherwise attached, see FIG. 6 as an exemplary embodiment). The pair of wires 74C can be a twisted pair in some embodiments. The pair of wires 74C can be generally perpendicular to a winding axis (e.g., a longitudinal axis) of the core 68C (e.g., a "T-sensor" or "T-shaped sensor"). In some embodiments, the pair of wires 74C can be configured at an angle not perpendicular to the longitudinal axis of the core 68C.

The transducer assembly 64C can also include a pair of protrusions 82. The pair of protrusions 82 can be any portion of the transducer assembly 64C that protrude from the transducer assembly 64C allowing the transducer assembly 64C to be coupled with, for example, an opening or slot (e.g., a receptacle) in a fixture or other structure (e.g., a transducer assembly receptacle 92 in FIGS. 7A-D). The opening/slot can allow the transducer assembly 64C to be aligned in a specific manner as the pair of protrusions 82 can couple with portions of the opening/slot (see FIGS. 7A-D and related discussion below). The alignment of the transducer assembly 64C can be precise due to the construction of the transducer assembly 64C and the opening/slot in the fixture, including the coupling of the protrusions 82 with the opening/slot in the fixture, which allows the direction of vectors of fields (e.g., magnetic fields) associated with the transducer assembly 64C. While FIG. 5 shows a pair of protrusions, some embodiments could have a single protrusion or more than two protrusions to be used for coupling and/or aligning the transducer assembly 64C with a receptacle. Because the pair of wires 74C can be coupled with the coil 66C at the intermediate portion and not the first end and/or the second end, the pair of wires 74C does not interfere with the protrusions and couple of the transducer assembly 64 with, for example, the opening/slot in the fixture, which allows for precise alignment of the transducer.

The coating 72C on and/or surrounding the core 68C can be any suitable material including for example, an adhesive, a polymer, (e.g., polyimide, fluorinated ethylene propylene, heat shrink (e.g., nylon, polyolefin), a metal, etc. The coating 72C can be used to create the size and/or shape of the sensor assembly. For example, the thicker the layer of the coating 72C (e.g., as measured radially from the core 68C) the larger the diameter of the core/coil/coating portion of the transducer assembly 64C. The coating 72C can cover all of the coil 66 or a portion of the coil 66. The coating 72C can be the same thickness (e.g., as measured radially from the core 68C) or it can have varying thickness at different portions along the core 68C (e.g., see FIG. 6 and related discussion below).

As described above, the position detection module can include, for example, a processor and a memory storing non-transitory computer-readable instructions, as discussed herein (e.g., as part of the ECU 42 in FIG. 1, or a separate processor and a separate memory, or a combination of the two). The ECU 42 may be programmed with a computer program (e.g., software) encoded on a computer-readable storage medium for assessing the distances between, for example, an electrode and one or more sensors. The instructions can be executable to compute, for example, movement and/or position(s) of the distal end (e.g., a tip electrode and/or one or more of the electrodes 34 of FIG. 1) of a catheter (e.g., the catheter 14 of FIG. 1) and a distal end of an introducer, the rate of change in the distances, or other characteristics related to the position of the distal end of the catheter in relation to the distal end of the introducer. The program can include code for calculating a value responsive to magnitudes of, for example, a voltage across a sensor (e.g., a sensor located on the catheter) and a drive coil (e.g., a transducer used to generate/emit a field and/or a signal). The magnitude of the voltage can be used to determine, for example, a distance between electrodes on a catheter, a position of a sensor on a catheter with respect to a another sensor (e.g., a sensor on a test fixture, a sensor on an introducer, etc.).

Figure 6:
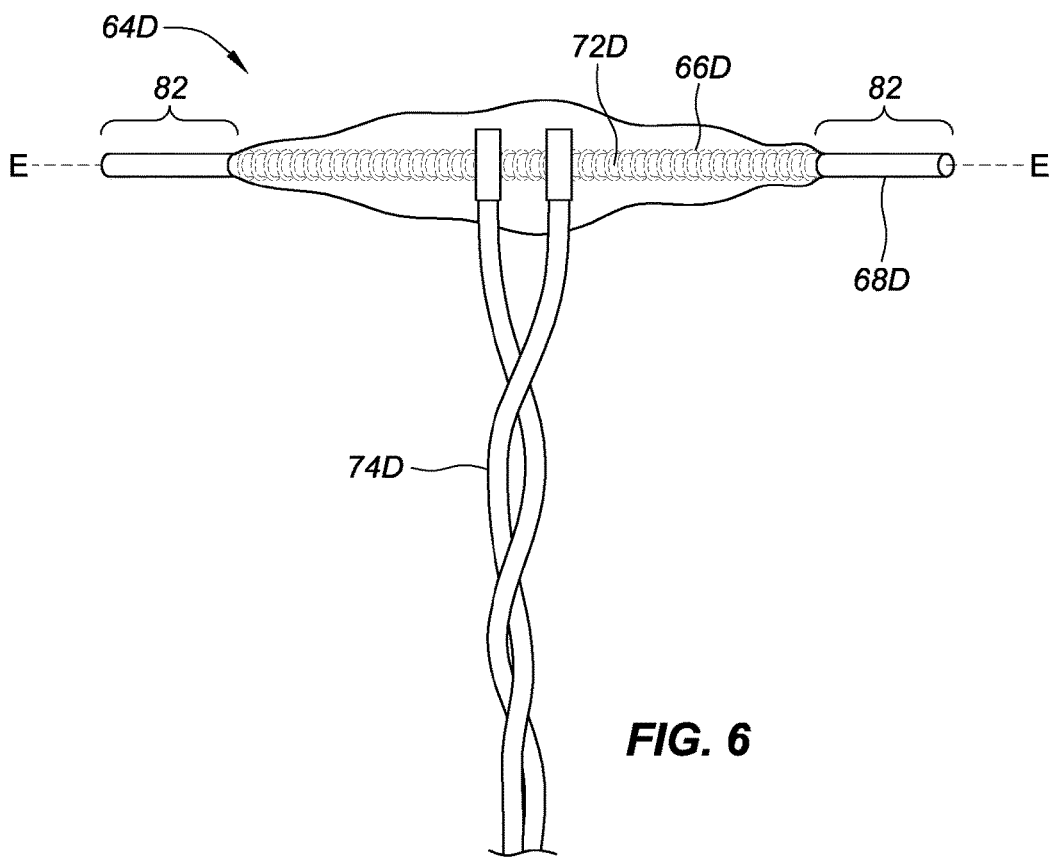
FIG. 6 is a schematic view of a transducer assembly that can be used for locating and/or tracking a position of a medical device, in accordance with embodiments of the present disclosure.

FIG. 6 is a schematic view of a transducer assembly that can be used for locating and/or tracking a position of a medical device, in accordance with embodiments of the present disclosure. The transducer assembly 64D can include a coil 66D, a core 68D, a coating 72D, and a pair of wires 74D. The coil 66D can have varying diameters in relation to a longitudinal axis of the core 64D, represented by the line E-E, as shown in FIG. 6. In some embodiments, the diameter (e.g., as measured radially from the core 62D) of the coil 66D can be variable as depicted. In other embodiments, the diameter of the coil 66D can be the same (e.g., see FIGS. 3 and 5 and related discussion).

The coating 72D on and/or surrounding the core 68C can be any suitable material including for example, an adhesive, a polymer, (e.g., polyimide, fluorinated ethylene propylene, heat shrink (e.g., nylon, polyolefin), a metal, etc. The coating 72D can be used to create the size and/or shape of the sensor assembly. For example, the thicker the layer of the coating 72D (e.g., as measured radially from the core 68D) the larger the diameter of the core/coil/coating portion of the transducer assembly 64D. The coating 72D can cover all of the coil 66D or a portion of the coil 66D. The coating 72C can be the same thickness (e.g., as measured radially from the core 68) or it can have varying thickness at different portions along the core 68D (e.g., see FIG. 6 and related discussion below).

In some embodiment, the transducer assembly 64D can be coupled with an elongate medical device (e.g., an introducer or a catheter sheath). When a distal end of a shaft (e.g., distal end 32) of a catheter (e.g., catheter 14 of FIG. 1) that includes one or more electrodes (e.g., electrodes 34) that are known distances from a sensor (e.g., the second sensor in FIGS. 2A-C) coupled with the catheter, the transducer assembly 64D can be used to determine a location of the catheter sensor (e.g., the second sensor in FIGS. 2A-C) and therefore the electrodes on the catheter with respect to the sensor on the introducer (e.g., a drive coil/the second sensor in FIGS. 2A-C). As the distance between the drive coil (e.g., transducer assembly 64D) and the distal end of the introducer can be known (e.g., predetermined or measured), the position of the sensor (e.g., the second sensor in FIGS. 2A-C) on the catheter and, therefore, the position of the electrodes can be determined by, for example, an electronic control unit (e.g., ECU 42 in FIG. 1). This arrangement can be used to determine a position for electrodes and/or sensors on a catheter when portions of the catheter are concealed inside the introducer (e.g., where the introducer shields/inhibits the electrodes and/or other sensors (e.g., magnetic coils) from providing information about the location/position of the catheter with respect to the introducer.

The embodiment of the transducer assembly 64D shown in FIG. 6 omits the tube 70A included in the sensor assembly 62A of FIG. 4. The lack of the tube eliminates the issue described above related to offset/and or misalignment that can cause up to 0.50 of angulation between the longitudinal axis of the tube 70A and the longitudinal axis of the coil 66A and the core 68A which can lead to errors in determining a location/position of a second sensor (e.g., transducer assembly 64A) with respect to a first transducer (a drive coil). The lack of the tube allows for easier (e.g., more accurate) placement and/or alignment of the transducer assembly 64D to align the longitudinal axis of the transducer assembly 64D (represented by line E-E) with a path of travel for another sensor (e.g., the first sensor 58 of FIGS. 2A-C).

FIG. $7A_1$ is a top and partial cross-sectional view of an apparatus 84 for measuring sensor spacing on an elongate medical device, where the apparatus includes a transducer assembly 64E that can be used for generating a field used for measuring the spacing on the elongate medical device, in accordance with embodiments of the present disclosure. The apparatus (or fixture) 84 can include the transducer assembly 64E and a fixture 84.

The fixture 84 can be configured to temporarily couple with a portion of a catheter (e.g., catheter 14 of FIG. 1). In one embodiment, the fixture 84 can include a tube 86. The tube 86 can be arranged so the longitudinal axis of the transducer assembly 64E, represented by the line F-F, is perpendicular to a longitudinal axis of the tube, represented by the line G-G. The fixture can also include a base plate 88. The tube 86 can be removably coupled with the base plate 88. The base plate 88 can include a mounting hole 90 and a transducer assembly receptacle 92. The mounting hole 90 can be used to secure the base plate 88 (e.g., to a surface or another apparatus).

The transducer assembly receptacle 92 can be configured to couple with a transducer assembly (e.g., the transducer assemblies 64A-E). The transducer assembly receptacle 92 can include portions (e.g., slots, notches, recesses, openings, etc.) that accept the protrusions (e.g., the protrusions 82) of the transducer assembly (e.g., the transducer assemblies 64A-E) to provide alignment of the transducer assembly (e.g., perpendicular to tube 86). The protrusions 82 can be, for example, portions of the core (e.g., the core 68C/68D of FIG. 5/FIG. 6. The transducer assembly receptacle 92 can have portions that are closely sized to match portions of the transducer assembly 64. For example, the transducer assembly receptacle 92 could have portions that are close in size to the protrusions 82 (e.g., close tolerance to provide a precise fit, such as an interference fit) to allow for precise alignment of the protrusions 82, which in turn, allows for precise alignment of the transducer assembly 64 with respect to the fixture 84. In some embodiments, the transducer assembly receptacle can be adjustable (e.g., via set screws or other features that allow for fine adjustment of the alignment of the transducer assembly).

The transducer assembly 64E can be a sensor similar to those described herein, where the transducer assembly 64E can generate a signal and/or field (e.g., a magnetic field) that can be used to, for example, determine the position and/or location of a sensor on a catheter. The transducer assembly 64E can be coupled with the fixture 80. As discussed herein, the transducer assembly 64E can be mounted to the fixture 80 so that the longitudinal axis (line F-F) of the transducer assembly 64E is perpendicular to the longitudinal axis of a tube 86, represented by the line G-G.

The tube 86 can have an open end 94 and a closed end 96. The tube 86 can have a diameter 98 to accommodate the insertion of a portion of a catheter (e.g., catheter 14 of FIG. 1) into the open end 94 of the tube 86. The tube 86 can include, in some embodiments, portions of the tube wall 100 can be modified (e.g., cut out for windows, translucent sections of material, etc.) to facilitate viewing of the catheter while inserted into the tube 86 (not shown). The tube 86 can be removably coupled with the base plate 88 to allow for tubes of different diameter to be coupled with the base plate to accommodate catheters with different diameters. The tube 86 may be sized to allow insertion of the catheter (e.g., catheter 14 of FIG. 1) into the tube 86, but to limit excess movement of the catheter in the tube (e.g., to limit and/or minimize misalignment of the catheter within the tube with respect to the sensor assembly).

In some embodiments, the closed end 96 can be a conductive material (e.g., a metal). The catheter (e.g., catheter 14 of FIG. 1) can be inserted until a distal top of the catheter is in contact with the closed end 96. With a conductive surface on the catheter distal end (e.g., a tip electrode) in contact with the conductive material of the closed end 96, contact of the catheter and the closed end 96 can be verified using, for example, a multimeter or similar tool, or a circuit can be used with an audible alert. Once contact with the catheter and the closed end 96 is confirmed, the catheter can be moved back (e.g., pulled out of the tube 86) until the sensor assembly (e.g., sensor assembly 63E) is aligned with the center of the sensor on the catheter (e.g., sensor 58A as shown in FIG. 7C below). The distance the catheter is moved back is the distance from the tip of the catheter to the center of the sensor (e.g., sensor 58A as shown in FIG. 7C.

Because the tube 86 can be arranged with the longitudinal axis of the transducer assembly 64E (line F-F) aligned (e.g., perpendicular) with respect to a longitudinal axis of the tube 86 (represented by the line G-G), a magnetic field generated by the transducer assembly 64E can be used to determine a location and/or spacing of sensors (e.g., electrodes, magnetic coils, etc.) on a catheter. The catheter can be inserted into the open end 94 of the tube 86 and moved through the tube 86. Longitudinal movement of the catheter (e.g., catheter 14 of FIG. 1) can generate a signal (e.g., a voltage measured across a sensor coupled with the catheter) and the signal can indicate a longitudinal position of the sensor coupled with the catheter (e.g., the distance of the sensor from a tip, a distance between a first sensor and a second sensor, etc.).

Rotational movement of the catheter (e.g., rotating clockwise or counter-clockwise about the longitudinal axis of the catheter) can cause variations in the signal. The variations in the signal can be used to determine an orientation of the sensor on the catheter, including, for example, locations of multiple sensors the same distance from the tip, but spaced about a circumference of the catheter. For example, if two magnetic sensors (e.g., a first sensor and a second sensor) are located on the catheter, where the first sensor generates a higher voltage, the first sensor is closer to the drive coil and the second sensor is further from the drive coil. If the catheter is rotated 180°, then the second sensor will generate a higher voltage and the first sensor will generate a lower voltage. This concept can be used to determine the rotational location/position of sensors with respect to the drive coil.

The fixture 84 can be used during the manufacturing process (e.g., to check, calibrate, identify, etc.) of the catheter (e.g., catheter 14 of FIG. 1) to assist with desired placement of sensors on the catheter. The fixture can also be used to identify the spacing and/or location of sensors to, for example, provide information to be used in medical procedures (e.g., catheters that are purchased from other sources and used after manufacturing). In some embodiments, the fixture 84 can be used to determine distances between various electrodes and/or sensors of unknown spacing on a catheter. In another embodiment, the fixture 84 can be used to confirm distances between various sensors and electrodes on a catheter. For example, once the spacing and/or location of sensors is determined using the information described herein, data regarding the sensor locations can be input and/or used by a system (e.g., ECU 42 of FIG. 1, etc.) to be used during a medical procedure that incorporates the catheter that was measured. This distance/location information can be useful for situations where portions of a catheter (e.g., catheter 14 of FIG. 1) are shielded by an introducer during a procedure, preventing the use of other positioning determinations as described above.

FIG. 7A$_2$ is a side view of the fixture 84 of FIG. 7A$_1$, in accordance with embodiments of the present disclosure. As described above, the fixture 84 can include the tube 86 coupled with the base plate 88. The tube 86 can have the open end 94 and the closed end 96. The base plate can include a mounting hole 90 and a transducer assembly receptacle 92. As shown in FIG. 7A$_2$ the transducer assembly receptacle 92 can be an integral part of the base plate 88. In some embodiments, the transducer assembly receptacle 92 can be a separate element that is coupled with the base plate 88 (e.g., coupled with a surface of the base plate 88 instead of a cavity formed in the base plate 88).

FIG. 7B is a schematic view of the fixture 84 of FIGS. 7A$_1$ and 7A$_2$ with an exemplary catheter 14A that includes a sensor 58A mounted on the catheter 14A, where the catheter 14A is movable relative to the transducer assembly 64E, in accordance with embodiments of the present disclosure. Similar to the discussion above related to FIGS. 7A$_1$ and 7A$_2$, the fixture 84 can include a transducer assembly 64E (e.g., a first transducer or a drive coil), a tube 86, where the tube 86 is coupled with the base plate 88 and the base plate 88 can include a mounting hole 90. The tube 86 can include the open end 94 and the closed end 96 and the diameter 98 of the tube 86 can be sized to allow the catheter 14A to be inserted into the tube 86. The tube 86 can be removably coupled with the base plate as discussed above.

The catheter 14A can be inserted into an open end 94 of a tube 86 so that a first sensor 58A (e.g., a magnetic coil) is in a first position (e.g., a position that places the first sensor 58 to the right (as shown in FIG. 7B) in the tube with respect to the transducer assembly 64E (represented by the line F-F)). Similar to the discussion related to FIG. 2C above, a voltage, as measured across the first sensor 58A, can be positive for the first sensor 58A (e.g., a larger positive voltage value as you move the first sensor 58A further to the right of the line F-F). See the discussion above related to FIG. 2C for more information.

As described herein, a position detection module can compute, for example, movement and/or position(s) of the catheter 14A based on, for example, changes in voltage measured across the sensor 58A. The distances between the sensor 58A and an electrode 34A (e.g., a tip electrode) and electrodes 34B and 34C of a catheter 14A can be known (e.g., measured prior to and/or during use). With the distances between the sensor 58A and the electrodes 34A-C known, the current position, past positions, distance between positions, the rate of change in the distances, or other characteristics related to the position of the distal end of the catheter in relation to the distal end of the introducer can be tracked. The program (e.g., instructions) can include code (instructions) for calculating a value responsive to magnitudes of, for example, a voltage across a sensor (e.g., a sensor located on the catheter) and a drive coil (e.g., a transducer used to generate a field and/or a signal). The value can be used with information related to distances between various parts of the catheter 14A (e.g., the electrodes 34A-C, additional sensors, etc.) to determine a position of the catheter 14A with respect to the transducer assembly 64E. The position of the catheter 14A can then be output to a display (e.g., display 40). The position information (e.g., a position data) can be in the form of data (e.g., coordinates, distances, etc.) and/or in a graphical representation of the catheter 14A as it moves.

Changes in voltage can be a characteristic of the relationship of changes in distance between a first sensor (e.g., transducer assembly 64E) and a second sensor (e.g., the sensor 58A). Other characteristics that can be used include, for example, measuring changes in any one or more of a current, a magnetic field strength, a magnetic flux density, and/or other properties related to sensors and/or fields generated by the first sensor as described herein.

FIG. 7C is a schematic view of the apparatus 84 of FIGS. 7A$_1$ and 7A$_2$ with the exemplary catheter 14A of FIG. 7B, where the catheter 14A has moved relative to the transducer assembly 64E, in accordance with embodiments of the present disclosure. In FIG. 7C, the catheter 14A is moved longitudinally in the tube 86 to a second position (e.g., from the open end 94 towards the closed end 96), where the first sensor 58A (e.g., a magnetic coil) is centered (as shown in FIG. 7C) on the longitudinal axis of the transducer assembly 64E (represented by the line F-F). Similar to the discussion related to FIG. 2B above, a voltage, as measured across the first sensor 58A, can be zero for the first sensor 58A when the first sensor 58A is in the second position. See the discussion above related to FIG. 2B for more information.

FIG. 7D is a schematic view of the fixture 84 of FIGS. 7A$_1$ and 7A$_2$ with the exemplary catheter 14A of FIGS. 7B-C, where the catheter 14A has moved relative to the transducer assembly 64E, in accordance with embodiments of the present disclosure. The catheter 14A can be inserted further into the tube 86 (e.g., from the open end 94 towards the closed end 96) so that a first sensor 58A (e.g., a magnetic coil) is in a third position of (e.g., a position that places the first sensor 58 to the left (as shown in FIG. 7D) of the longitudinal axis of the transducer assembly 64E (represented by the line F-F)). Similar to the discussion related to FIG. 2A above, a voltage, as measured across the first sensor 58A, can be positive for the first sensor 58A (e.g., a larger positive voltage value as you move the first sensor 58A further to the left of the line F-F). See the discussion above related to FIG. 2A for more information.

Another embodiment (not shown) similar to FIGS. 7B-D can include a sensor assembly (e.g., transducer assembly 64E) coupled with an introducer. Similar to the arrangement shown in FIGS. 7B-D, movement of a catheter (e.g., catheter 14A) within the introducer would allow for a position detection module to track the location/position of the catheter as it moves within the introducer. For example, the transducer assembly 64E of FIGS. 7B-D could be coupled with an introducer, where a longitudinal axis of the sensor assembly (e.g., longitudinal axis represented by line F-F in FIGS. 7B-D) is perpendicular to the longitudinal axis of the introducer, which would be the path of travel for a catheter in the introducer (e.g., similar to the catheter 14A traveling through the tube 86 as shown in FIGS. 7B-D). The position of electrodes and/or sensors on the catheter could be determined as described herein.

FIG. 8 shows an exemplary method for detecting the position of a sensor on an elongate medical device, consistent with embodiments of the present disclosure. A method 110 can include positioning a catheter at an open end of a tube on a fixture at a block 112, inserting the catheter into the open end of the tube at a block 114, emitting a field from a first transducer at a block 116, measuring a signal at a first sensor on the catheter while moving the catheter in a longitudinal direction at a block 118, analyzing the signal, by an ECU comprising a processor, from the first sensor at a block 120, determining, by the ECU, a position of the first sensor based on the signal at a block 122, and outputting, by the ECU, the position to a display at a block 124, in accordance with embodiments of the present disclosure.

Portions of the method can be repeated for catheters that have more than one sensor. For example, after the first sensor's position is detected as the catheter is moved in the longitudinal direction, the method can repeat by measuring the signal at the second sensor on the catheter while moving the catheter in the longitudinal direction; analyzing the signal, by an ECU comprising a processor, from the second sensor, determining, by the ECU, the position of the second sensor based on the signal, and outputting, by the ECU, the position to the display.

FIG. 9 is a schematic view of an optic-magnetic registration plate (OMRP), consistent with embodiments of the present disclosure. An OMRP 130 can include a plate 132 coupled with a plurality of objects 134 and a plurality of transducer assemblies 136 and a plurality of transducer assembly receptacles 138. Each of the plurality of objects 134 can comprise, for example, one or more radiopaque fiducial markers. The plurality of objects 134 can either be located at a known position or the positions can be determined (e.g., by the system 10 of FIG. 1). The plurality of objects 134 can be any suitable shape (round, square, oval, triangular, etc.) and made from any suitable material to be visible in the system being used (e.g., radiopaque for systems using x-rays, etc.). The plurality of objects 134 can be arranged in any suitable pattern. Each of the plurality of objects 134 can be the same size or the sizes can vary.

The plurality of transducer assemblies 136 can be located at any suitable known location on the OMRP 130 with respect to the plurality of objects 134. In one embodiment, the plurality of transducer assemblies 136 can include three transducer assemblies, $136_A$, $136_B$, $136_C$, that can be arranged so that a longitudinal axis of each of the transducer assemblies form an angle of, for example, 0°, 45° and 90° with respect to the longitudinal axis of the OMRP 130. The orientations of the three of transducer assemblies $136_A$, $136_B$, $136_C$ can be any three angles with respect to the longitudinal axis of the OMRP 130 (e.g., 5°, 50° and 95°; 10°, 45° and 90°; 0°, 60° and 90°; 30°, 60° and 100°, etc.) as provided by the available locations of the transducer assembly receptacle 138 locations on the OMRP 130. The OMRP 130 can have multiple transducer assembly receptacle 138 locations (e.g., more than three) to allow for the transducer assemblies 136 to be placed in various locations on the OMRP 130 to allow for different configurations of the transducer assemblies 136. In some embodiments the transducer assemblies 136 can be coupled with the OMRP via the transducer assembly receptacle (e.g., emitter assembly $136_A$ as shown in FIG. 9; also similar to the transducer assembly receptacle 92 shown in FIGS. 7B-D and described above) or the transducer assemblies can be coupled with the OMRP at locations without transducer assembly receptacles (e.g., transducer assemblies $136_B$ and $136_C$) using other suitable techniques (e.g., adhesive, etc.). For simplicity, a conductive connector (e.g., a pair of wires 74) is not shown connected to each of the transducer assemblies $136_A$, $136_B$, and $136_C$ (see above for related discussion).

A system (e.g., the system 10 of FIG. 1) can be used to detect a location of the plurality of objects 134 (e.g., using x-ray images, fluoroscopy, ultrasound, or any other suitable method) and a location of magnetic sensors (e.g., the transducer assemblies $136_A$, $136_B$, $136_C$, first sensor 58 (FIG. 2A), etc.). An ECU (e.g., ECU 42) can use known relationships between detected items to co-register two coordinate systems. For example a first coordinate system can be relative to the system 10 (of FIG. 1) and a second coordinate system can be relative to a body (e.g., the body 12 of FIG. 1). The known relationships can either be measured by the system 10 or previously determined such as, for example, a set distance between detected items, such as a fixed feature on a plate (e.g., the fixed distances between the plurality of objects 134 on the OMRP 130). Additional information can be found in U.S. application no. 2013/0272592 (application Ser. No. 13/977,438), which is hereby incorporated by reference as if set forth fully herein.

Although at least one embodiment of an apparatus for detecting catheters to introducers has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements and can also include elements that are part of a mixture or similar configuration. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system comprising:
a first transducer assembly with a first longitudinal axis, the first transducer assembly comprising a core, a conductive winding, and a conductive connector electrically coupled with the conductive winding, wherein the core is parallel with the first longitudinal axis;
a catheter with a second longitudinal axis, wherein the catheter comprises
a first sensor, and
a plurality of electrodes, where a location of a second sensor is known in relation to each of the plurality of electrodes;
where the first longitudinal axis of the transducer assembly is perpendicular with the second longitudinal axis of the catheter; and
an electronic control unit electrically coupled to the first transducer assembly and the first sensor and operable to do the following:
(A) generate a magnetic field using the first transducer assembly;
(B) measure a first signal from the first sensor, wherein the first signal varies based on a position of the first sensor along the second longitudinal axis in relation to the magnetic field generated by the first transducer assembly;
(C) analyze the first signal to determine a relative position of the catheter along the second longitudinal axis based on the location of the first sensor;
(D) generate a relative position information for the catheter using the analysis of the first signal.

2. The system of claim 1, further comprising an introducer, where the first transducer assembly is coupled with the introducer.

3. The system of claim 1, further comprising a fixture, where the fixture comprises
a base plate;
a transducer assembly receptacle allowing the transducer assembly to be coupled with the base plate;
a tube with a third longitudinal axis removably coupled with the base plate, the tube comprising a closed end and an open end, wherein the open end is configured to accept a distal end of the catheter, wherein the third longitudinal axis of the tube is perpendicular to the first longitudinal axis of the transducer assembly.

4. The system of claim 1, where the catheter further comprises a second sensor and the electronic control unit is further operable to do the following:
measure a second signal from the second sensor, wherein the second signal varies based on a position of the second sensor in relation to the magnetic field generated by the first transducer assembly,
evaluate the second signal to determine a characteristic of the signal for the first sensor and the second signal for the second sensor,
correlate the characteristic of the signal to a position of the first sensor and the second signal to the second sensor,
determine a relative position of the catheter along the second longitudinal axis based on the position of the first sensor and the second sensor.

5. The system of claim 4, wherein the characteristic of the signal comprises one or more of a change in a voltage, a change in a current, a change in a magnetic field strength, and a change in a magnetic flux density.

6. The system of claim 1, wherein the electronic control unit is further operable to:
output the relative position to a display.

7. The system of claim 1, wherein the first transducer assembly further comprises a protrusion.

8. The system of claim 7, wherein the protrusion comprises a portion of the core.

9. A method for detecting a position of a sensor on an elongate medical device, comprising:
positioning a catheter at a first location along a first longitudinal axis,
emitting a field from a first transducer with a second longitudinal axis, where the first longitudinal axis is perpendicular with the second longitudinal axis,
moving the catheter to a second position along the longitudinal axis,
measuring a signal, by an electronic control unit comprising a processor, at a first sensor on the catheter while moving the catheter along the longitudinal axis from the first position to the second position within the field,
analyzing the signal, by the electronic control unit, from the first sensor, and
determining, by the electronic control unit, a position data of the first sensor based on the signal.

10. The method of claim 9, further comprising:
outputting, by the electronic control unit, the position data to a display.

11. The method of claim 9, further comprising:
measuring, by an electronic control unit comprising a processor, the signal at a second sensor on the catheter while moving the catheter along the longitudinal axis,
analyzing, by the electronic control unit, the signal from the second sensor,
determining, by the electronic control unit, the position data of the second sensor based on the signal, and
outputting, by the electronic control unit, the position data to the display.

12. The method of claim 9, wherein the determining further comprises a position of the first sensor with respect to one or more electrodes proximate the sensor.

* * * * *